(12) United States Patent
Fischer et al.

(10) Patent No.: US 8,501,235 B2
(45) Date of Patent: *Aug. 6, 2013

(54) USE OF DICALCIUM PHOSPHATE ANHYDRIDE POWDER

(75) Inventors: Erhard Fischer, Ingelheim (DE); Gerhard Scheuer, Nieder-Olm (DE); Jurgen Meven, Mainz (DE); Stefan Mallmann, Heidesheim (DE); Silke John, Ginsheim (DE)

(73) Assignee: Chemische Fabrik Budenheim KG, Budenheim (DE)

( * ) Notice: Subject to any disclaimer, the term of this patent is extended or adjusted under 35 U.S.C. 154(b) by 225 days.

This patent is subject to a terminal disclaimer.

(21) Appl. No.: 12/706,985

(22) Filed: Feb. 17, 2010

(65) Prior Publication Data

US 2010/0144894 A1    Jun. 10, 2010

Related U.S. Application Data

(63) Continuation of application No. 10/332,106, filed as application No. PCT/DE01/02484 on Jun. 29, 2001, now Pat. No. 7,691,410.

(30) Foreign Application Priority Data

Jul. 4, 2000 (DE) .................. 100 32 434

(51) Int. Cl.
- *A61K 9/14* (2006.01)
- *A61K 9/20* (2006.01)
- *A61K 9/48* (2006.01)

(52) U.S. Cl.
USPC ........... 424/489; 424/451; 424/464; 424/465

(58) Field of Classification Search
None
See application file for complete search history.

(56) References Cited

U.S. PATENT DOCUMENTS

| | | | |
|---|---|---|---|
| 4,743,274 A * | 5/1988 | Ozawa et al. ............. | 51/309 |
| 4,752,457 A | 6/1988 | Toriyana et al. | |
| 5,055,307 A * | 10/1991 | Tsuru et al. ............. | 424/493 |
| 7,045,105 B2 | 5/2006 | Lagow | |
| 2005/0031682 A1 | 2/2005 | Cucala Escoi et al. | |

FOREIGN PATENT DOCUMENTS

| | | | |
|---|---|---|---|
| EP | 0210661 A1 | | 2/1987 |
| EP | 0210661 A1 | * | 2/1987 |
| EP | 1008353 A1 | | 6/2000 |
| FR | 2220474 A | * | 11/1974 |

OTHER PUBLICATIONS

Doldan et al, "Dicalcium phosphate dihydrate and anhydrous dicalcium phosphate for direct compression: a comparative study", International Journal of Pharmaceutics, 124, 1995, pp. 69-74.

* cited by examiner

*Primary Examiner* — Susan Tran

(74) *Attorney, Agent, or Firm* — Dinsmore & Shohl LLP

(57) ABSTRACT

Dicalcium phosphate anhydride powder of which at least 50% by weight is of a grain size of between 45 and 150 μm, a maximum of 50% by weight is of a grain size of <45 μm and a maximum of 5% by weight is of a grain size >150 μm and which has a bulk density of between 1000 and 1500 g/l and a specific surface area of <5 m²/g is used for direct tabletting or capsule filling of pharmaceutical preparations.

7 Claims, No Drawings

USE OF DICALCIUM PHOSPHATE ANHYDRIDE POWDER

CROSS-REFERENCE TO RELATED APPLICATIONS

This application is a continuation of U.S. patent application Ser. No. 10/332,106 filed Aug. 15, 2003 now U.S. Pat. No. 7,691,410 entitled USE OF DICALCIUM PHOSPHATE ANHYDRIDE POWDER, which is a National Stage Entry of International Application No. PCT/DE01/02484 filed Jun. 29, 2001, published as WO 02/02082 A2, entitled USE OF DICALCIUM PHOSPHATE ANHYDRIDE POWDER, which claims foreign priority to DE 100 32 434.7 filed Jul. 4, 2000.

BACKGROUND

Dicalcium phosphate dihydrate is used to a great extent as a carrier substance in the pharmaceutical industry, but the range of use thereof is limited to active substances which are not water-sensitive as under unfavourable conditions the dihydrate can already slowly separate off water from a temperature of 40° C. Therefore the use of dicalcium phosphate anhydride acquired increasing attraction as a carrier substance for drug forms, in particular for the direct tabletting of pharmaceutical products.

Dicalcium phosphate anhydride is generally produced by the neutralisation of phosphoric acid with a basic calcium compound, for example calcium hydroxide or calcium carbonate, at a temperature above 60° C. At lower temperatures dicalcium phosphate dihydrate or a mixture of dicalcium phosphate dihydrate and anhydride is produced. The dicalcium phosphate anhydride generally occurs in the form of fine crystals which are crushed in mills to form powder. The products obtained in that way are usually of an average grain size of smaller than 20 µm and are of a bulk density of between 500 and 900 g/l. Because of the high degree of fineness and the poor trickle flow capability which this involves, those anhydride products cannot be directly tabletted but have to be granulated prior to use in order to ensure an adequate flow capability which is required for uniformly filling the dies of the tabletting machines.

In order to avoid those disadvantages, a switch was made to using coarse-grain dicalcium phosphate anhydride for direct tabletting. By way of example U.S. Pat. No. 4,707,361 describes a coarse-grain dicalcium phosphate anhydride powder for tabletting with a grain size of at least 90% greater than about 44 µm and at least 95% smaller than about 420 µm and with a specific surface area of greater than 5 m$^2$/g. That powder is produced by dehydrating dicalcium phosphate dihydrate.

DE-A-4 122 960 describes a process for producing coarse-grain dicalcium phosphate anhydride powder, in which at least 95% are of a grain size of over 45 µm and the mean grain diameter thereof is in the range of between 130 and 150 µm. That powder which is intended for direct tabletting is produced by a procedure whereby dilute phosphoric acid is provided at a temperature of between 70 and 90° C. and lime solution and further phosphoric acid are added, maintaining a pH-value of between 3 and 4.5. The pH-value is then adjusted to between 5.5 and 6.8 with lime solution.

Finally EP-A-0 644 156 describes, for drugs, cosmetics and foodstuffs, a dicalcium phosphate with a low water of hydration content and a specific surface area of between 20 and 60 m$^2$/g, a bulk weight of a maximum of 200 g/l and a grain size of the primary particles of between 0.1 and 5 µm and a grain size of the agglomerates of between 2 and 10 µm. Manufacture is effected by precipitation from phosphoric acid and an alkaline calcium compound in the presence of an organic complexing compound and granulation by spray drying.

Now the object of the present invention is to obtain a dicalcium phosphate anhydride powder with superior trickle properties, by means of which, particularly in the direct tabletting of pharmaceutical preparations, increased amounts of calcium can be introduced into the preparation.

SUMMARY OF THE INVENTION

In accordance with the invention dicalcium phosphate anhydride powder of which at least 50% by weight is of a grain size of between 45 and 150 µm, a maximum of 50% by weight is of a grain size of <45 µm and a maximum of 5% by weight is of a grain size >150 µm and which has a bulk weight of between 1000 and 1500 g/l and a specific surface area of <5 m$^2$/g, is used for the direct tabletting or capsule filling of pharmaceutical preparations.

Preferably use is made of a dicalcium phosphate anhydride powder with a bulk weight of between 1200 and 1400 g/l, preferably such a powder with a specific surface area <2 m$^2$/g.

DETAILED DESCRIPTION

The dicalcium phosphate anhydride powder used in accordance with the invention is distinguished by a particularly high bulk weight and, in spite of the relatively high degree of fineness, by a very good trickle flow characteristic. For that reason this powder is particularly suitable for direct tabletting without preceding granulation and introduces a larger amount of calcium into the resulting preparation, than other anhydride powders, without the volume of the drug form greatly increasing. The product is also excellently suited to filling hard and soft gelatine capsules.

The grain size distribution of the dicalcium phosphate anhydride powders used in accordance with the invention can be achieved by purely mechanical processes by sieving off fractions of given grain sizes and specifically mixing together given proportions of various grain size fractions. The above-mentioned properties of the dicalcium phosphate anhydride powder used in accordance with the invention can however also be set by suitable reaction implementation.

EXAMPLES

Example 1 and Comparative Example 1

The two test formulations each comprise 99% by weight of dicalcium phosphate anhydride and 1% by weight of magnesium stearate.

The dicalcium phosphate anhydride used in accordance with the invention had the following properties:

| | |
|---|---|
| bulk weight | 1300 g/l |
| specific surface area | 1.5 m$^2$/g |
| sieve analysis through 45 µm: | 35% wt |
| 45-150 µm: | 63% wt |
| over 150 µm: | 2% wt |

The dicalcium phosphate anhydride in accordance with the comparative example had the following properties:

| | |
|---|---|
| bulk weight | 750 g/l |
| specific surface area | 15 m²/g |
| sieve analysis | |
| through 45 μm: | 3% wt |
| 45-150 μm: | 42% wt |
| over 150 μm: | 55% wt |

The two test formulations were used to press tablets having the following tabletting parameters:

| | |
|---|---|
| pressing force | 40 kN |
| tabletting speed | 20,000 tablets/h |
| tablet diameter: | 10 mm |
| filling height of the dies: | so set that a tablet thickness of 3.0 mm is achieved. |

Result:

| | Formulation according to the invention | Formulation according to the comparative example |
|---|---|---|
| Tablet weight | 515 mg | 440 mg |
| mg Ca/tablet | 150 mg | 128 mg |
| Tablet thickness | 3.0 mm | 3.0 mm |
| Tablet hardness | 52 N | 112 N |

With the same tablet thickness, a considerably higher calcium content per tablet is achieved when using the dicalcium phosphate anhydride powder according to the invention.

Example 2 and Comparative Example 2

The two test formulations each comprise 60% by weight of dicalcium phosphate anhydride, 39% by weight of MCC (microcrystalline cellulose) and 1% by weight of magnesium stearate.

The dicalcium phosphate anhydride used in accordance with the invention has the following properties:

| | |
|---|---|
| bulk weight | 1300 g/l |
| specific surface area | 1.5 m²/g |
| sieve analysis | |
| through 45 μm: | 35% wt |
| 45-150 μm: | 63% wt |
| over 150 μm: | 2% wt |

The dicalcium phosphate anhydride used in the comparative example had the following properties:

| | |
|---|---|
| bulk weight | 750 g/l |
| specific surface area | 15 m²/g |
| sieve analysis | |
| through 45 μm: | 3% wt |
| 45-150 μm: | 42% wt |
| over 150 μm: | 55% wt |

The two test formulations were used to press tablets having the following tabletting parameters:

| | |
|---|---|
| pressing force | 40 kN |
| tabletting speed | 20,000 tablets/h |
| tablet diameter: | 10 mm |
| filling height of the dies: | so set that a tablet weight of 325 mg was achieved. |

Result:

| | Formulation according to the invention | Formulation according to the comparative example |
|---|---|---|
| Tablet weight | 325 mg | 325 mg |
| mg Ca/tablet | 77 mg | 77 mg |
| Tablet thickness | 2.2 mm | 2.5 mm |
| Tablet hardness | 134 N | 123 N |

With the same amount of calcium in the two tablets those using the dicalcium phosphate anhydride powder employed in accordance with the invention were of a considerably smaller tablet thickness.

What is claimed is:

1. A method of using a dicalcium phosphate anhydride powder comprising:
   providing a dicalcium phosphate anhydride powder having a bulk weight of between 1000 and 1500 g/l, wherein at least 50% by weight of said powder is of a grain size of between 45 and 150 μm, wherein said powder has a specific surface area of <5 m²/g; and
   direct tabletting at least one pharmaceutical product with said dicalcium phosphate anhydride powder.

2. The method as claimed in claim 1 wherein said dicalcium phosphate anhydride powder comprises a bulk weight of between 1200 and 1400 g/l.

3. A method of using a dicalcium phosphate anhydride powder comprising:
   providing a dicalcium phosphate anhydride powder having a bulk weight of between 1000 and 1500 g/l, wherein at least 50% by weight of said powder is of a grain size of between 45 and 150 μm, wherein said powder has a specific surface area of <5 m²/g; and
   capsule filling at least one pharmaceutical product with said dicalcium phosphate anhydride powder.

4. The method as claimed in claim 3 wherein said dicalcium phosphate anhydride powder comprises a bulk weight of between 1200 and 1400 g/l.

5. A method of using a dicalcium phosphate anhydride powder comprising:
   providing a dicalcium phosphate anhydride powder by direct precipitation, said powder having a bulk weight of between 1000 and 1500 g/l; wherein at least 50% by weight of said powder is of a grain size of between 45 and 150 μm, wherein said powder has a specific surface area of <5 m²/g; and
   direct tabletting or capsule filling at least one pharmaceutical product with said dicalcium phosphate anhydride powder.

6. A tabletted pharmaceutical product comprising dicalcium phosphate anhydride powder, said powder having a bulk weight of between 1000 and 1500 g/l; wherein at least 50% by weight of said powder is of a grain size of between 45 and 150 μm, wherein said powder has a specific surface area of <5 m²/g.

7. A pharmaceutical product comprising a capsule filled with dicalcium phosphate anhydride powder, said powder having a bulk weight of between 1000 and 1500 g/l; wherein at least 50% by weight of said powder is of a grain size of between 45 and 150 μm, wherein said powder has a specific surface area of <5 $m^2/g$.

\* \* \* \* \*